United States Patent
Ho et al.

(10) Patent No.: US 11,161,795 B2
(45) Date of Patent: Nov. 2, 2021

(54) METHOD FOR PREPARATION OF INSENSITIVE HIGH EXPLOSIVE

(71) Applicant: National Chung-Shan Institute of Science and Technology, Taoyuan (TW)

(72) Inventors: Chan-Yuan Ho, Hsinchu (TW); Tsair-Feng Lin, Taoyuan (TW); Yan-Lin Wang, New Taipei (TW)

(73) Assignee: National Chung-Shan Institute of Science and Technology, Taoyuan (TW)

( * ) Notice: Subject to any disclaimer, the term of this patent is extended or adjusted under 35 U.S.C. 154(b) by 609 days.

(21) Appl. No.: 16/197,373

(22) Filed: Nov. 21, 2018

(65) Prior Publication Data
US 2020/0039895 A1 Feb. 6, 2020

(30) Foreign Application Priority Data
Jul. 31, 2018 (TW) ................................. 107126800

(51) Int. Cl.
*C06B 25/34* (2006.01)
*C07D 257/04* (2006.01)

(52) U.S. Cl.
CPC ............ *C06B 25/34* (2013.01); *C07D 257/04* (2013.01)

(58) Field of Classification Search
CPC ....................................................... C06B 25/34
See application file for complete search history.

(56) References Cited

U.S. PATENT DOCUMENTS

| | | | |
|---|---|---|---|
| 9,296,664 B2 | 3/2016 | Klapotke | |
| 9,643,937 B1 | 5/2017 | Damavarapu | |
| 2005/0043539 A1* | 2/2005 | Gediya | C07D 417/12 546/269.7 |
| 2014/0171657 A1* | 6/2014 | Klapotke | C07D 257/04 548/251 |

FOREIGN PATENT DOCUMENTS

| | | |
|---|---|---|
| CN | 103524444 | 1/2014 |
| CN | 104277007 | 1/2015 |
| CN | 104829548 | 8/2015 |

OTHER PUBLICATIONS

Ju, "Improved synthesis of TKX-50",2015.
(Continued)

*Primary Examiner* — Aileen B Felton
(74) *Attorney, Agent, or Firm* — Winston Hsu

(57) ABSTRACT

The present invention provides a method for the preparation of an insensitive high enthalpy explosive Dihydroxylammonium 5,5'-bistetrazole-1,1'-diolate (TKX-50) in the presence of N,N-dimethylformamide, N,N-dimethylacetamide, or N-Methyl-2-pyrrolidone as a solvent via a four-step, one-pot reaction route to obtain a final product after four reaction steps. The more dangerous intermediate diazidoglyoxime may be solved by the one-pot method without the need of isolation. Further, the cyclization reaction is carried out in the presence of dropwisely added concentrated sulfuric acid to replace hydrochloric gas so no hydrochloric gas generator is needed to greatly reduce the amount of waste acid so as to effectively reduce the cost by avoiding using hydrochloric gas steel cylinders which require much safety equipment.

13 Claims, 6 Drawing Sheets

(56) References Cited

OTHER PUBLICATIONS

Bi, "Synthesis and Properties of Dihydroxylammonium 5,5'-bistetrazole-1,1'-diolate", 2014.
Nicolich, "Dihydroxylammonium 5,5'-bis-tetrazole-1,1'-diolate (TKX-50) Synthesis and Lab Scale Characterization", 2014.
Golenko, "Optimization Studies on Synthesis of TKX-50", 2016.

* cited by examiner

METHOD FOR PREPARATION OF INSENSITIVE HIGH EXPLOSIVE

BACKGROUND OF THE INVENTION

1. Field of the Invention

The present invention generally relates to a method for the preparation of an insensitive high explosive. In particular, the present invention is directed to a method for the preparation of an insensitive high explosive Dihydroxylammonium 5,5'-bistetrazole-1,1'-diolate (TKX-50) by changing a solvent and a reagent to greatly reduce the generation of a waste acid and to simplify the procedure steps for the synthesis to be suitable for the scale-up production for use in the organic synthesis technique field.

2. Description of the Prior Art

In recent years, energetic materials of tetrazole structures becomes the hot spot of the research of insensitive high energetic materials because of the high density, high enthalpy, high gas yield, low sensitivity, good thermal stability and nitrogen gas ($N_2$) to be the major decomposed product.

In 2001, Tselinskii et al. synthesized a new bistetrazole compound, namely 1,1'-dihydroxy-5,5'-bistetrazole ($H_2$DHBT). Later, BI Fu-Giang et al. also synthesized the compound and verified the structure and thermal stability of the compound. With the further study of ionic liquids, energetic ionic salts were introduced into the design of single-compound explosives. In 2012, Universitat München reported the Dihydroxylammonium 5,5'-bistetrazole-1,1'-diolate (TKX-50). After tests, it has a density up to 1.918 g/cm$^3$ at 100 K, thermal stability of decomposition is 221° C., an impact sensitivity of 20 J, friction sensitivity of 120 N, and an electrostatic sensitivity of 0.1 J. Its calculated detonation velocity is 9698 m/s and its detonation pressure is 42.4 GPa to denote that TKX-50 is a promising insensitive high explosive to be well developed.

U.S. Pat. No. 9,296,664 B2 of Thomas M. Klapötke (Universitat München) proposes two different approaches to synthesize TKX-50. The first approach is an early method to firstly synthesize 5,5'-bistetrazole and the obtained 5,5'-bistetrazole is then oxidized by potassium persulfate. However, the oxidation step is prone to side reactions with difficult product separation. The poor yield of 5,5'-Bistetrazole-1,1'-diol is 13%. The second approach is a new synthesis method (a three-step, one-pot reaction route) which is illustrated in FIG. 1.

The yield of the synthesis route as shown in FIG. 1 is 74.6% (based on dichloroglyoxime (DCG)). In addition, N-methyl-2-pyrrolidone (NMP) may be used to replace N,N-dimethylformamide (DMF) with 85.1% yield (based on dichloroglyoxime (DCG)). The above route is a three-step, one-pot method. If the yield of the first two steps (glyoximation and chlorination reactions) is 90% respectively, the total yield proposed by Thomas M. Klapötke is 60.4% (in DMF) and 68.9% (in NMP), respectively. There is the disadvantage such as adding diethyl ether to serve as the solvent for the cyclization reaction. It is known for its high volatilizing property. When it volatilized dry, the mixture is prone to isolate the highly friction and impact sensitive compound diazidoglyoxime. Further, this route requires de-pressured distillation to remove water and N,N-dimethylformamide so it is only applicable to the laboratory scale because it is complicate.

CN 104829548A of Beijing Institute of Technology proposes an improved method (a four-step, one-pot reaction route) as shown in FIG. 2. At first glyoxime is synthesized with 86% yield, then followed by a four-step, one-pot reaction to synthesize TKX-50 with 87% yield (based on glyoxime). The total yield is 74.82% when the glyoximation reaction is involved. The disadvantages are as follows. There are two sources of hydrochloric gas which is used for the cyclization reaction. The first is the gas generator which produces a lot of waste acid. The second is a hydrochloric gas steel cylinder but it requires the same safety equipment as that of a chlorine steel cylinder to meet the legal regulations of toxic substances.

CN 104277007 A of Hubei Institute of Aerospace Chemotechnology proposes another improved route (a three-step, one-pot reaction route) as shown in FIG. 3. Dichloroglyoxime is used as the starting material to synthesize TKX-50 with 85% yield (based on dichloroglyoxime) via a three-step, one-pot route. If the yield of the first two steps (glyoximation and chlorination reactions) is 90% respectively, the total yield of the synthesis method is 68.85%. Alcohols serve as the solvent of the reactions and the cyclization reaction is carried out in the presence of concentrated sulfuric acid. The involved ingredients and the procedures to add concentrated sulfuric acid to replace hydrochloric gas may avoid the disadvantages of pumping hydrochloric gas but the subsequent treatments do not carry out the neutralization so it is less safe to operate because there is concern about the generation of hydrogen azide. This is a three-step, one-pot route which is more complicated than a four-step, one-pot route and dichloroglyoxime is additionally processed to be disadvantageous for the future scale-up.

Nanjing University of Science and Technology proposed another improved route as shown in FIG. 4. The improved route mainly resides in the disuse of the toxic solvent N,N-dimethylformamide (DMF) and the diazidation reaction as well as the cyclization reaction is carried out in a one pot reaction with 88% yield. This is a more complicated route and diethyl ether is used as the extract solvent for the extract of diazidoglyoxime in the procedures. Diethyl ether itself is relatively dangerous because it is highly volatile and the precipitated primary explosive, diazidoglyoxime, is prone to explosion and hazard when the solvent is vaporized.

CN 103524444 A of Beijing Institute of Technology proposed another improved route (a three-step, one-pot reaction) as shown in FIG. 5. The proposed improved route mainly resides in the use of water as the solvent with the addition of chlorine gas for the chlorination reaction with 60% yield. Because chlorine gas is highly viscous and prone to linger in the pipelines, the pipelines need purging with nitrogen gas to purge residual gas after the reaction is completed. Additional equipment for the safety protocol and for the detection of chlorine gas is therefore needed.

Xi'an Modern Chemistry Research Institute proposed another improved route (a two-step, one-pot reaction) as shown in FIG. 6. Dichloroglyoxime is used as the starting material to obtain TKX-50 after a cyclization reaction and an ion exchange reaction with 93.4% yield. The cost is high because lithium salts are formed by adding lithium hydroxide in the reaction. Further in this route the cyclization reaction is carried out in the presence of diethyl ether to serve as the solvent to which hydrochloric gas is added. Highly volatile diethyl ether itself is relatively dangerous so the reaction time is relatively longer and is disadvantageous for the industrious process because the reaction is carried out under lower temperature. The precipitated primary explosive, diazidoglyoxime, is also prone to explosion and hazard when the solvent is vaporized.

U.S. Army Research Development and Engineering Center (ARDEC) developed another process (a four-step, one-pot reaction route) as shown in FIG. 7. The process is an early route proposed by ARDEC. It mainly resides in using dioxane in the cyclization reaction to replace more dangerous ether but the drawbacks are as follows. Chlorine gas is used as a chlorinating agent in the chlorination reaction, and the reaction temperature is between −30° C.~−40° C. so the low temperature reaction is disadvantageous for the future industrious process. Later the process was improved and patented as U.S. Pat. No. 9,643,937. The chlorinating agent in FIG. 7 is changed to be NCS/DMF with 71.3% yield via a four-step, one-pot reaction route. The disadvantages are as follows. There are two sources of hydrochloric gas which is used for the cyclization reaction. The first is the gas generator which produces a lot of waste acid. The second is a hydrochloric gas steel cylinder but it requires the same safety equipment as that of a chlorine steel cylinder to meet the legal regulations of toxic substances.

After the evaluation of the approaches of Klapotke and of Tselinskii, Golenko et al. of Russian Academy of Science in 2016 proposed another improved route (a four-step, one-pot reaction) in Chinese Journal of Chemistry as shown in FIG. 8. Glyoxime is used as the starting material to obtain TKX-50 with 74% yield via a four-step, one-pot reaction route. It mainly resides in using dioxane in the cyclization reaction to replace more dangerous ether but the disadvantages are as follows. There are two sources of hydrochloric gas which is used for the cyclization reaction. The first is the gas generator which produces a lot of waste acid. The second is a hydrochloric gas steel cylinder but it requires the same safety equipment as that of a chlorine steel cylinder to meet the legal regulations of toxic substances.

Table 1 shows the information of the above-mentioned eight routes of synthesis.

TABLE 1

| Sources | Chlorination and cyclization reaction | Vaporization of solvent | Total yield (%) | Remarks |
| --- | --- | --- | --- | --- |
| Universität München | $Cl_2$/EtOH, HCl/Ether | DMF/$H_2O$ vaporized | 60.4 (DMF) 68.9 (NMP) | three-step, one-pot reaction |
| Beijing Institute of Technology | NCS/DMF, HCl/DMF | No | 74.82 (DMF) | four-step, one-pot reaction |
| Hubei Institute of Aerospace Chemotechnology | 98% $H_2SO_4$ for cyclization | No | 68.85 | three-step, one-pot reaction (single alcohol used) |
| Nanjing University of Science and Technology | $Cl_2$/EtOH, HCl/Ether | No | 63.0 | two-step, one-pot reaction (no toxic used) |
| Beijing Institute of Technology | $Cl_2$/$HCl_{(aq)}$, HCl/Ether | No | 48.6 | three-step, one-pot reaction |
| Xi'an Modern Chemistry Research Institute | HCl/Ether for cyclization | No | 66.2 | two-step, one-pot reaction (DAG filtered, LiOH for neutralization) |
| ARDEC | NCS/DMF, HCl/Dioxane | DMF/Dioxane vaporized | 64.0 | four-step, one-pot reaction |
| Russian Academy of Science | NCS/NMP, HCl/Dioxane | Dioxane/$H_2O$ vaporized | 66.6 | four-step, one-pot reaction |

Golenko et al. also published a report of the synthesis of TKX-50 in Chinese Journal of Chemistry. They use Lewis acids ($BF_3 \cdot Et_2O$, $ZnCl_2$, $TiCl_4$ or $AlCl_3$) and sulfuric acid to carry out the reaction for the observation of the influences of different Lewis acids on the cyclization reaction. The results are listed in Table 2.

TABLE 2

| Entry | Conditions | Yield % |
| --- | --- | --- |
| 1 | DMF, dry 1,4-dioxane, 0° C., 4 mol · $L^{-1}$ HCl in 1,4-dioxane | 15 |
| 2 | DMF, 0° C., 12 mol · $L^{-1}$ HCl aq. | 9 |
| 3 | DMF, 0° C., 12 mol · $L^{-1}$ HCl aq., $HCl_{(g)}$ | 24 |
| 4 | DMF, 0° C., 12 mol · $L^{-1}$ HCl aq., $H_2SO_4$ 98% | 0 |
| 5 | DMF, 0° C., aq. $H_2SO_4$ 50% | 0 |
| 6 | DMF, 0° C., $HCl_{(g)}$ | 13 |
| 7 | DMF, 0° C., $BF_3 \cdot Et_2O$ | 0 |
| 8 | DMF, 0° C., $ZnCl_2$ | 0 |
| 9 | DMF, 0° C., $TiCl_4$ | 0 |
| 10 | DMF, 0° C., $AlCl_3$ | 0 |

The results listed in Table 2 indicate that all the yields are poor when different acids are used to replace hydrochloric acid gas for the cyclization reaction. If no hydrochloric acid gas is used, the cyclization reaction is not possible so the yields are 0 (Entries 5, 7, 8, 9 and 10). Even if the hydrochloric acid is present, the cyclization reaction is still not possible so the yields are 0 when concentrated sulfuric acid is used to replace hydrochloric gas (Entries 3 and 4). The results listed in Table 2 also shows that concentrated sulfuric acid exhibits a complete inhibiting effect to the function of hydrochloric acid which is capable of promoting the cyclization reaction instead of an accelerating effect (Entry 5) on the cyclization reaction in the presence of sulfuric acid and in the presence of N,N-dimethylformamide (DMF) to serve as a solvent for the cyclization reaction. Accordingly, the yields are still 0 (Entries 2 and 4) in the presence of hydrochloric acid when concentrated sulfuric acid is added.

In view of the above routes, they have advantages and disadvantages. After researches, the inventors of the invention propose another novel and beneficiary method for the preparation of an insensitive high explosive. The method has mild reaction conditions, has high yield, is not hazardous, is simple to operate, and reduces waste acids.

SUMMARY OF THE INVENTION

In the light of the disadvantages of prior art, the main objective of present invention resides in providing a method for the preparation of an insensitive high explosive. By using glyoxal as a starting material, Dihydroxylammonium 5,5'-bistetrazole-1,1'-diolate can be synthesized in the presence of a suitable solvent and in the presence of concentrated sulfuric acid. The method employs mild reaction conditions, which is not dangerous, is easy to operate, reduces waste acids, and has high yield to prepare TKX-50 which has ideal explosive performance to be applicable to the national defense field, for example to serve as warhead main charge and a major propellant. It is surprising to the inventors of the present invention to find out that concentrated sulfuric acid exhibits a satisfying promotion to the mild cyclization reaction in the presence of N,N-dimethylformamide, dimethylacetamide or N-methyl-2-pyrrolidone which serves as a solvent to obtain acceptable yields. The one pot reaction route which is designed by the inventors of the present invention gets rid of the bias of the experiment data proposed by prior art which teaches away the use of concentrated sulfuric acid to promote the cyclization reaction in the presence of N,N-dimethylformamide as a solvent and shows unexpected results.

In order to achieve the above objective, in accordance with one embodiment of the present invention, a method for the preparation of an insensitive high explosive via a four-step, one-pot reaction route is provided with the steps as follows:

(A) performing chlorination reaction: dissolving glyoxime in N,N-dimethylformamide or in dimethylacetamide before adding N-chlorosuccinimide and cooling to 0° C.~10° C. then carrying out the reaction for several hours when warming up to suitable temperature;

(B) performing azidation reaction: adding sodium azide with cooling to −5° C.~5° C. to carry out the reaction for 1~4 hours at 25° C.~50° C.;

(C) performing cyclization reaction: adding concentrated sulfuric acid and carrying out the reaction for 14~16 hours at suitable temperature before cooling, adding 40% sodium hydroxide aqueous solution to adjust a pH value, then filtrating and washing the products with water to obtain 1,1'-dihydroxy-5,5'-bistetrazole sodium salt tetrahydrate (BTO-Na.4H$_2$O); and (D) performing ion exchange reaction: adding hydroxylammonium chloride aqueous solution dropwisely to carry out the reaction for hours at suitable temperature after dissolving the obtained 1,1'-dihydroxy-5,5'-bistetrazole sodium salt tetrahydrate in adequate water to obtain Dihydroxylammonium 5,5'-bistetrazole-1,1'-diolate (TKX-50) after cooling, filtrating and washing the products with water.

Preferably, N,N-dimethylformamide or dimethylacetamide is used as a solvent, and a weight ratio of the added solvent to the glyoxime may be 5~15:1.

Preferably, the weight ratio of the added solvent to the glyoxime may be 10:1.

Preferably, for the chlorination reaction a mole ratio of the added N-chlorosuccinimide to the glyoxime may be 1~3:1 to carry out the reaction at a temperature range of 25° C.~45° C.

Preferably, for the chlorination reaction a mole ratio of the added N-chlorosuccinimide to the glyoxime may be 1.9~2:1 to carry out the reaction at a temperature range of 25° C.~35° C.

Preferably, for the azidation reaction a mole ratio of the added sodium azide to the glyoxime may be 1~3:1 to carry out the reaction at a temperature range of 0° C.~20° C.

Preferably, for the azidation reaction a mole ratio of the added sodium azide to the glyoxime may be 2:1 to carry out the reaction at a temperature range of 0° C.~10° C.

Preferably, for the cyclization reaction a mole ratio of the added concentrated sulfuric acid to the glyoxime may be 7~15:1 to carry out the reaction at a temperature range of 50° C.~70° C.

Preferably, for the cyclization reaction a mole ratio of the added concentrated sulfuric acid to the glyoxime may be 10.5~12.6:1 to carry out the reaction at a temperature range of 65° C.~70° C.

Preferably, 40% sodium hydroxide aqueous solution is added dropwisely to adjust the pH value to be 9 or more.

Preferably, 40% sodium hydroxide aqueous solution is added dropwisely to adjust the pH value to be 10.

Preferably, for the ion exchange reaction a weight ratio of the 1,1'-dihydroxy-5,5'-bistetrazole sodium salt tetrahydrate (BTO-Na.4H$_2$O) to the water may be 1:13~23 and a concentration of 30%~50% of hydroxylammonium chloride aqueous solution is added dropwisely to carry out the reaction at a temperature range of 60° C.~70° C.

Preferably, for the ion exchange reaction a weight ratio of the 1,1'-dihydroxy-5,5'-bistetrazole sodium salt tetrahydrate (BTO-Na.4H$_2$O) to the water may be 1:18~19 and a concentration of 40%~45% of the hydroxylammonium chloride aqueous solution is added dropwisely to carry out the reaction at a temperature range of 65° C.~67° C.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
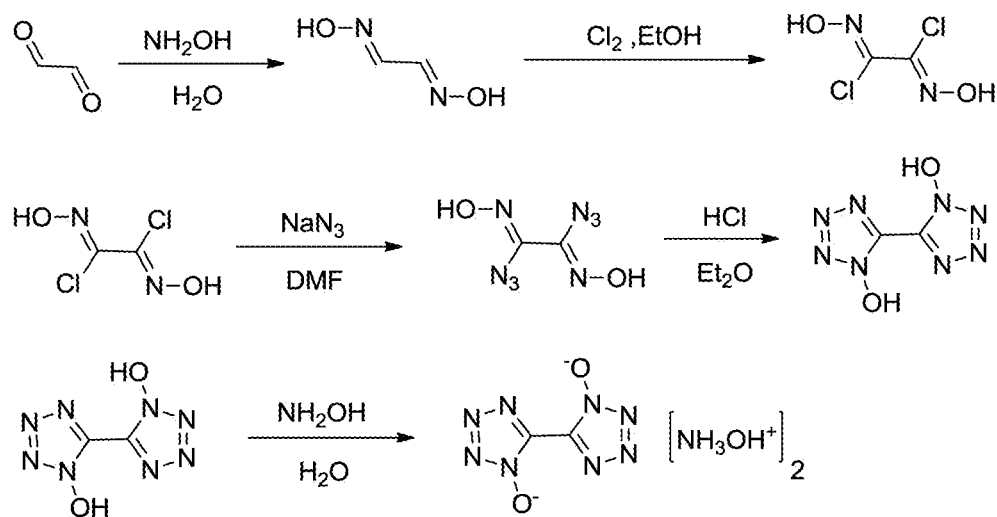
FIG. 1 illustrates that Thomas M. Klapotke (Universität München) proposes two different approaches to synthesize TKX-50 (a three-step, one-pot reaction).
Figure 2:
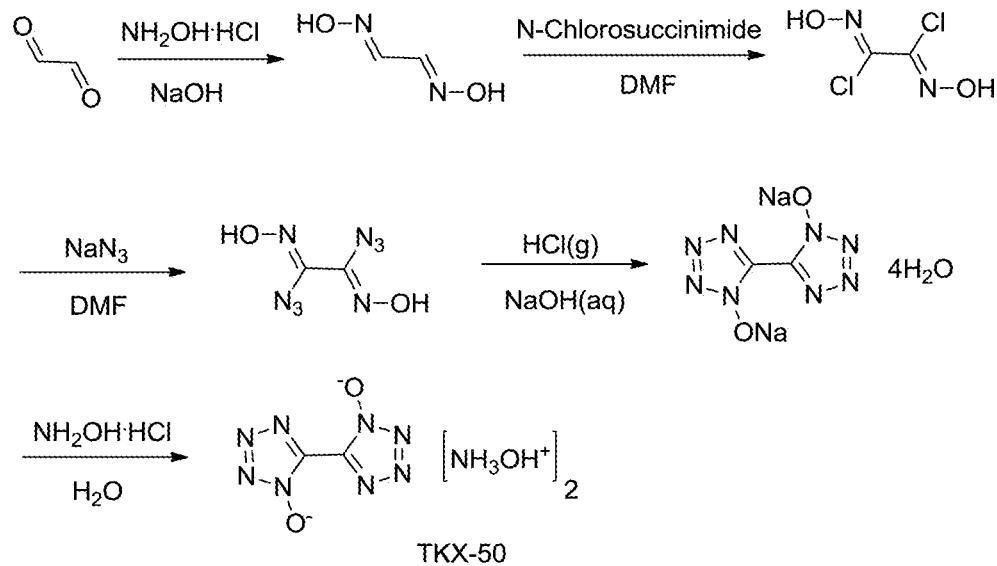
FIG. 2 illustrates that CN 104829548A of Beijing Institute of Technology proposes an improved method (a four-step, one-pot reaction).
Figure 3:
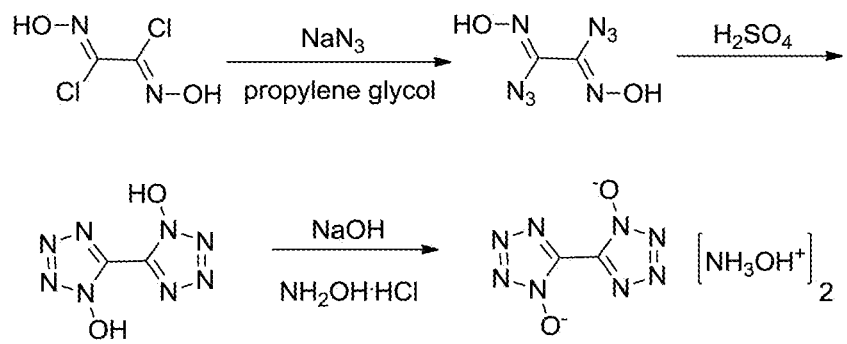
FIG. 3 illustrates that CN 104277007 A of Hubei Institute of Aerospace Chemotechnology proposes another improved route (a three-step, one-pot reaction).
Figure 4:
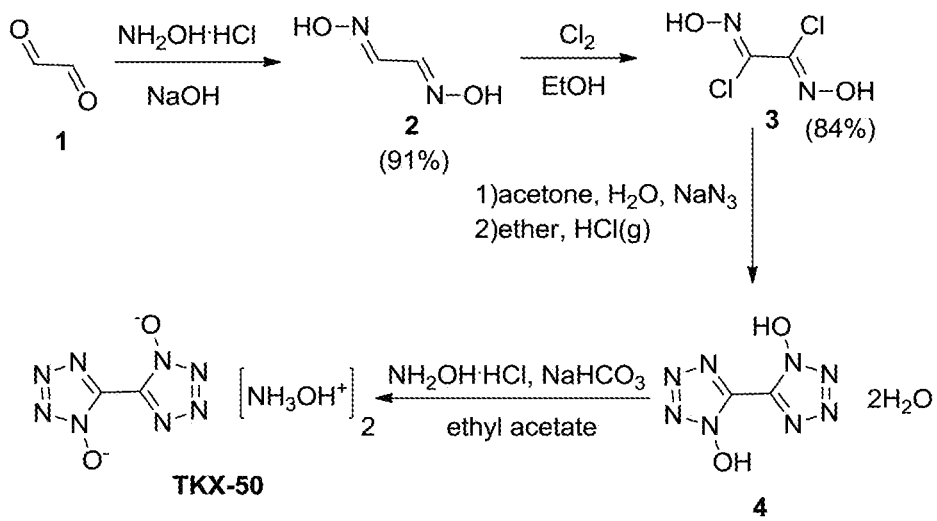
FIG. 4 illustrates that Nanjing University of Science and Technology proposed another improved route.
Figure 5:
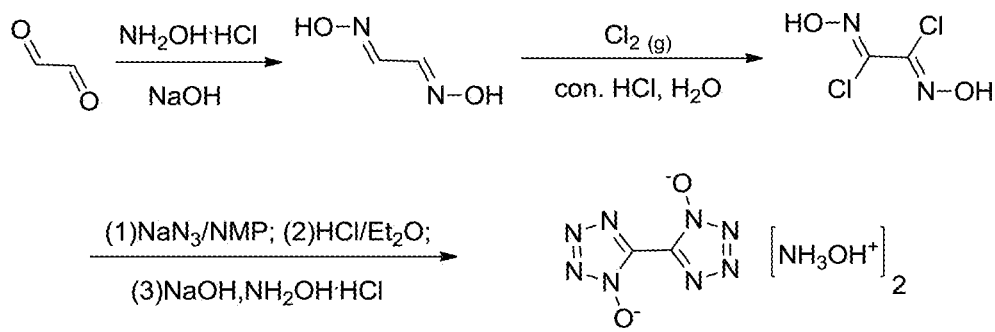
FIG. 5 illustrates that CN 103524444 A of Beijing Institute of Technology proposed another improved route.
Figure 6:
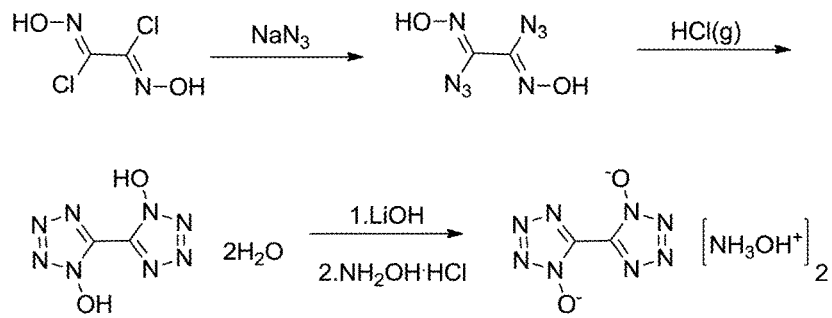
FIG. 6 illustrates that Xi'an Modern Chemistry Research Institute proposed another improved route (a two-step, one-pot reaction).
Figure 7:
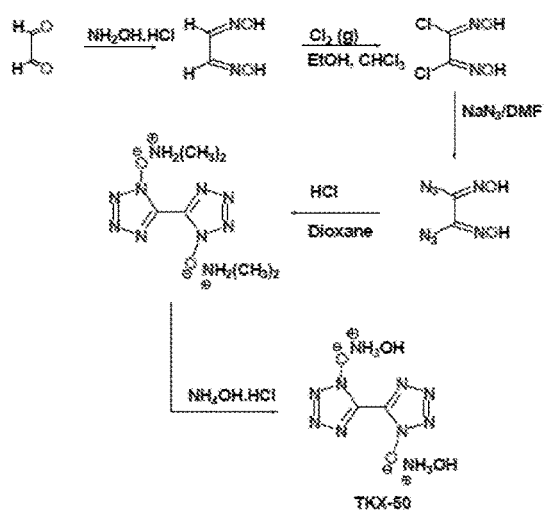
FIG. 7 illustrates that U.S. Army Research Development and Engineering Center (ARDEC) developed another process (a four-step, one-pot reaction).
Figure 8:
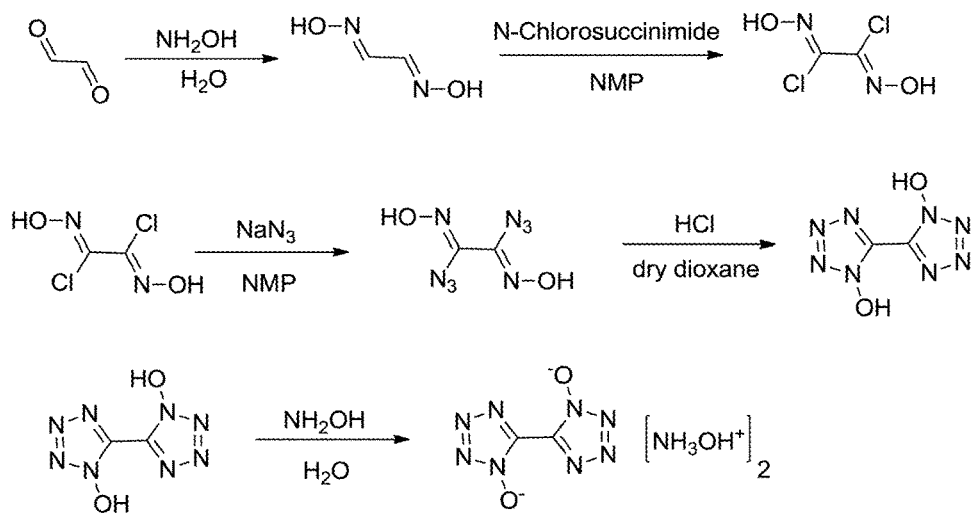
FIG. 8 illustrates that Russian Academy of Science proposed another improved route (a four-step, one-pot reaction).
Figure 9:
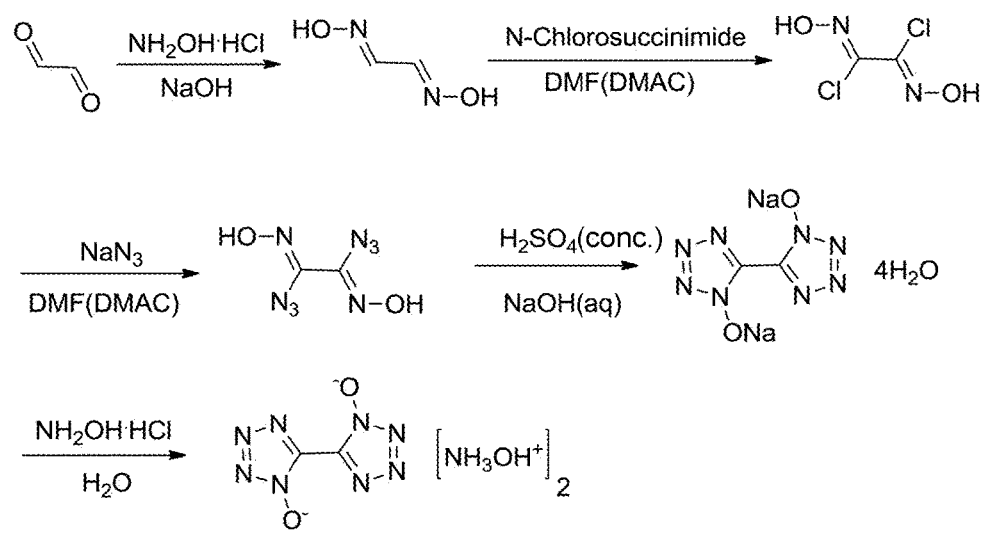
FIG. 9 illustrates a method for the preparation of an insensitive high enthalpy explosive via a four-step, one-pot reaction route of the present invention.

FIG. 9 illustrates a method for the preparation of an insensitive high enthalpy explosive via a four-step, one-pot reaction route of the present invention. The ingredients for the reaction includes glyoxal, sodium hydroxide, hydroxylammonium chloride, N-chlorosuccinimide, N,N-dimethylformamide (DMF), sodium azide, N, N-dimethylacetamide (DMAC), N-methyl-2-pyrrolidone (NMP) and sulfuric acid.

Example 1

To a 250 mL reactor hydroxylammonium chloride (37 gm) and water (40 gm) were added while stirring at room temperature. Sodium hydroxide (28.6%, 56 gm) was added dropwisely while cooling to 0° C. and glyoxal (40%, 38.6 gm) was added dropwisely to carry out the reaction at 0° C. for 20 minutes then warming up to 25° C. to carry out the reaction for 2 hours. Glyoxime was obtained after filtration with approximately 92% yield.

Then glyoxime (5 gm) was further dissolved in 50 mL of N,N-dimethylformamide (DMF) and N-chlorosuccinimide (15 gm) was added when cooled to 0° C.~10° C. The reaction was carried out for 1 hour when warmed up to 25° C.~35° C. After cooled to −5° C.~5° C., sodium azide (7.4 gm) was added to carry out the reaction for 3 hours. After concentrated sulfuric acid (36.6 gm) was added dropwisely to carry out the reaction at 60° C.~70° C. for 14 hours and cooled, a 40% sodium hydroxide aqueous solution was added dropwisely to adjust the pH value to be approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely at 60° C.~66° C. to carry out the reaction for 2 hours. Dihydroxylammonium 5,5'-bistetrazole-1,1'-diolate (TKX-50) was obtained after cooling and filtration with approximate 69% yield.

Example 2

Glyoxime (5 gm) was dissolved in 50 mL of N,N-dimethylformamide (DMF) and N-chlorosuccinimide (15 gm) was added when cooled to 0° C.~10° C. The reaction was carried out for 1 hour when warmed up to 25° C.~35° C. After cooled to −5° C.~5° C., sodium azide (7.4 gm) was added to carry out the reaction for 3 hours. After concentrated sulfuric acid (52.3 gm) was added dropwisely at 60° C. 70° C. to carry out the reaction for 15 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely to carry out the reaction at 60° C.~66° C. for 2 hours. Dihydroxylammonium 5,5'-bistetrazole-1,1'-diolate (TKX-50) was obtained after cooling and filtration with approximate 70% yield.

Example 3

Glyoxime (5 gm) was dissolved in 50 mL of N,N-dimethylacetamide (DMAC) and N-chlorosuccinimide (15 mg) was added when cooled to 0° C.~10° C. The reaction was carried out for 3 hours when warmed up to 30° C.~40° C. After cooled to −5° C.~5° C., sodium azide (7.4 gm) was added to carry out the reaction for 3 hours. After concentrated sulfuric acid (52.3 gm) was added dropwisely to carry out the reaction at 60° C.~70° C. for 15 hours and cooled, a 40% sodium hydroxide aqueous solution was added dropwisely to adjust the pH value to approximate to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely at ° C.~66° C. to carry out the reaction for 2 hours. Dihydroxylammonium 5,5'-bistetrazole-1,1'-diolate (TKX-50) was obtained after cooling and filtration with approximate 49% yield.

Example 4

Glyoxime (5 gm) was dissolved in 50 mL of N,N-dimethylacetamide (DMAC) and N-chlorosuccinimide (15 gm) was added when cooled to 0° C.~10° C. The reaction was carried out for 3 hours when warmed up to 35° C.~45° C. After cooled to −5° C.~5° C., sodium azide (7.4 gm) was added to carry out the reaction for 3 hours when warmed up to 10° C.~15° C. After concentrated sulfuric acid (52.3 gm) was added dropwisely to carry out the reaction at 60° C.~70° C. for 15 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely at 60° C.~66° C. to carry out the reaction for 2 hours. Dihydroxylammonium 5,5'-bistetrazole-1,1'-diolate (TKX-50) was obtained after cooling and filtration with approximate 61% yield.

Example 5

Glyoxime (5 gm) was dissolved in 50 mL of N,N-dimethylacetamide (DMAC) and N-chlorosuccinimide (15 gm) was added when cooled to 0° C.~10° C. The reaction was carried out for 3 hours when warmed up to 35° C.~45° C. After cooled to −5° C.~5° C., sodium azide (7.4 gm) was added then the reaction was carried out for 3 hours when warmed up to 15° C.~20° C. After concentrated sulfuric acid (52.3 gm) was added dropwisely to carry out the reaction at 60° C.~70° C. for 15 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely to carry out the reaction at 60° C.~66° C. for 2 hours. Dihydroxylammonium 5,5'-bistetrazole-1,1'-diolate (TKX-50) was obtained after cooling and filtration with approximate 44% yield.

Example 6

Glyoxime (5 gm) was dissolved in 50 mL of N,N-dimethylacetamide (DMAC) and N-chlorosuccinimide (15 gm) was added when cooled to 0° C.~10° C. The reaction was carried out for 3 hours when warmed up to 35° C.~45° C. After cooled to −5° C.~5° C., sodium azide (7.4 gm) was added then the reaction was carried out for 3 hours when warmed up to 5° C.~10° C. After concentrated sulfuric acid (57.7 gm) was added dropwisely to carry out the reaction at 60° C.~70° C. for 16 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely to carry out the reaction at 60° C.~66° C. for 2 hours. Dihydroxylammonium 5,5'-bistetrazole-1,1'-diolate (TKX-50) was obtained after cooling and filtration with approximate 65% yield.

Example 7

Glyoxime (5 gm) was dissolved in 50 mL of N,N-dimethylacetamide (DMAC) and N-chlorosuccinimide (15 gm) was added when cooled to 0° C.~10° C. The reaction was carried out for 3 hours when warmed up to 35° C.~45° C. After cooled to −5° C.~5° C., sodium azide (7.4 gm) was added then the reaction was carried out for 3 hours when warmed up to 5° C.~10° C. After concentrated sulfuric acid (62.8 gm) was added dropwisely to carry out the reaction at 60° C.~70° C. for 14 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely to carryout the reaction at 60° C.~66° C. for 2 hours. Dihydroxylammonium 5,5'-bistetrazole-1,1'-diolate (TKX-50) was obtained after cooling and filtration with approximate 72% yield.

Example 8

Glyoxime (5 gm) was dissolved in 50 mL of N-methyl-2-pyrrolidone (NMP) and N-chlorosuccinimide (15 gm) was added at 25° C.~35° C. The reaction was carried out for 1 hour when warmed up to 40° C.~50° C. After cooled to −5° C.~5° C., sodium azide (7.4 gm) was added then the reaction was carried out for 3 hours when warmed up to 5° C.~10° C. After concentrated sulfuric acid (62.8 gm) was added dropwisely to carry out the reaction at 60° C.~70° C. for 14 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and a hydroxylammonium chloride (42.3%, 23.44 gm) aqueous solution was added dropwisely to carryout the reaction at 60° C.~66° C. for 2 hours. Dihydroxylammonium 5,5'-Bistetrazole-1,1'-diolate (TKX-50) was obtained after cooling and filtration with approximate 44% yield.

Comparative Example 1

Glyoxime (5 gm) was dissolved in 50 mL of N,N-dimethylformamide (DMF) and N-chlorosuccinimide (15 gm) was added when cooled to 0° C.~10° C. The reaction was carried out for 1 hours when warmed up to 25° C.~35° C. and. After cooled to −5° C.~5° C., sodium azide (7.4 gm) was added then the reaction was carried out for 3 hours. After hydrochloric gas (hydrochloric gas was generated by slowly adding 65 gm of hydrochloric acid aqueous solution to 100 gm of concentrated sulfuric acid) was bubbled through for 1 hour and the reaction was carried out at 50° C.~60° C. for 12 hours and cooled, a 40% sodium hydroxide aqueous solution was added dropwisely to adjust the pH value to approximate 10 to obtain 1,1'-dihydroxy-5,5'-bistetrazole sodium salt tetrahydrate (BTO-Na.4H$_2$O) after filtration. The 1,1'-dihydroxy-5,5'-bistetrazole sodium salt tetrahydrate (BTO-Na.4H$_2$O) was dissolved in enough water and hydroxylammonium chloride (9.92 gm) and water (13.52 gm) were added dropwisely at 60° C.~66° C. to carry out the reaction for 2 hours. Dihydroxylammonium 5,5'-bistetrazole-1,1'-diolate (TKX-50) was obtained after cooling and filtration with approximate 70% yield. Because in COMPARATIVE EXAMPLE 1 hydrochloric acid gas was generated by adding hydrochloric acid aqueous solution dropwisely to concentrated sulfuric acid, it is confirmed that a lot of waste acid was produced in COMPARATIVE EXAMPLE 1 to be compared with the examples of the present invention.

Figure 10:
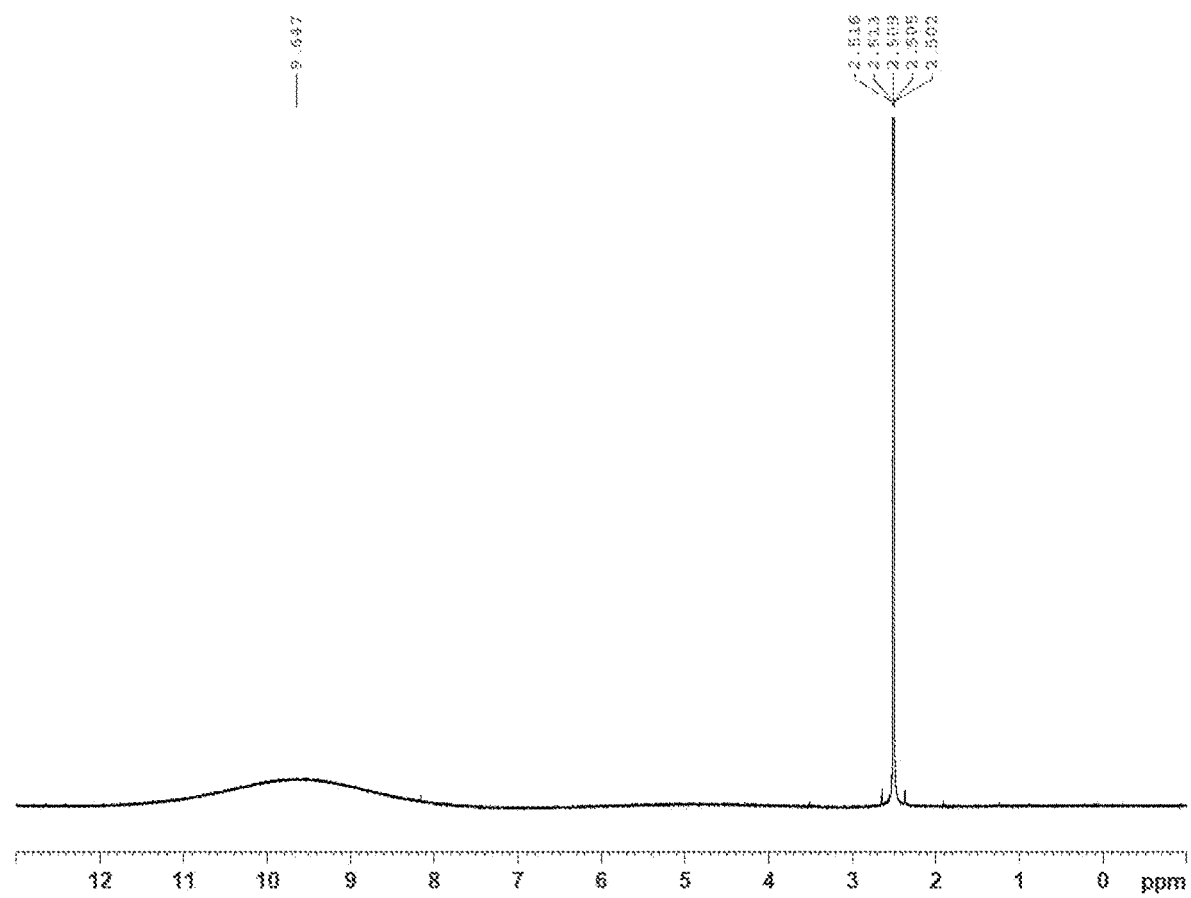
FIG. 10 illustrates the $^1$H NMR spectrum of Dihydroxylammonium 5,5'-bistetrazole-1,1'-diolate salt (TKX-50) which was prepared by the examples of the present invention in DMSO.
Figure 11:
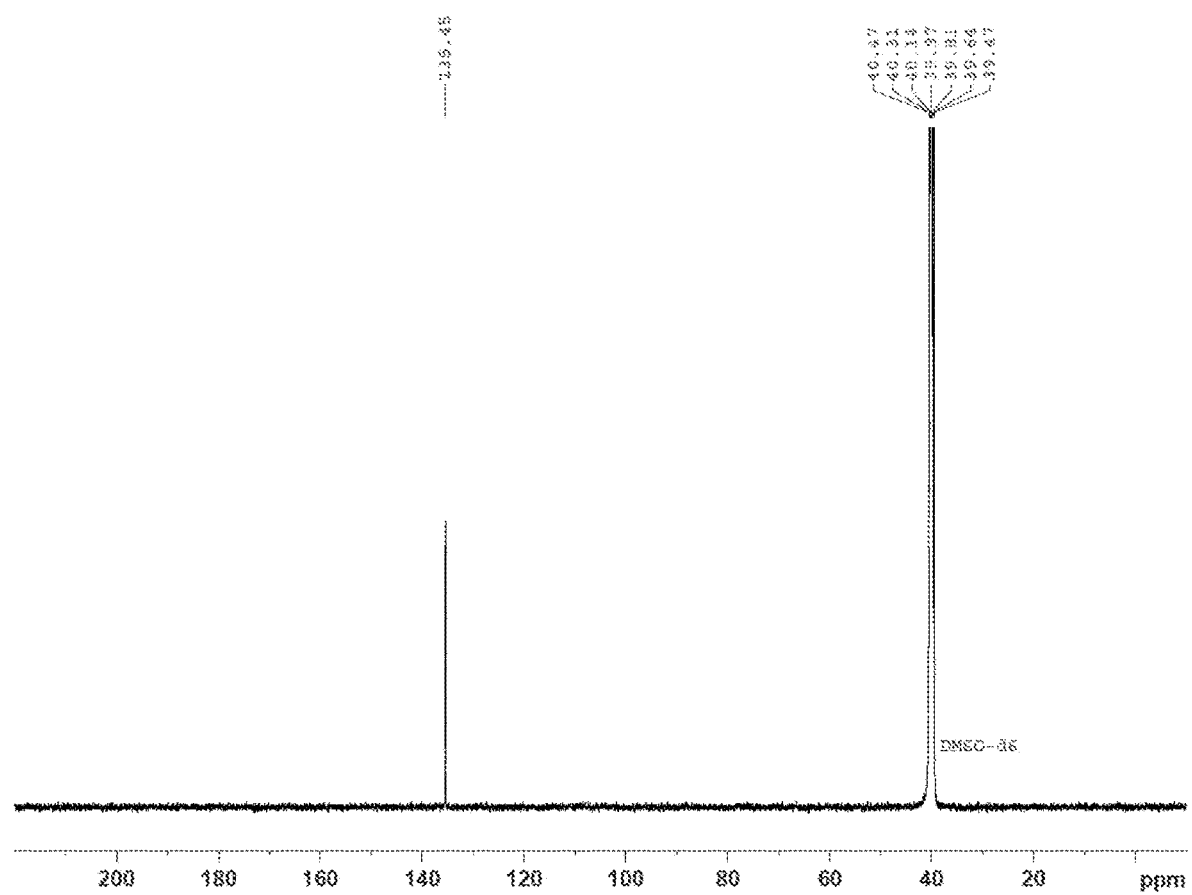
FIG. 11 illustrates the $^{13}$C NMR spectrum of Dihydroxylammonium 5,5'-bistetrazole-1,1'-diolate salt (TKX-50) which was prepared by the examples of the present invention in DMSO.
Figure 12:
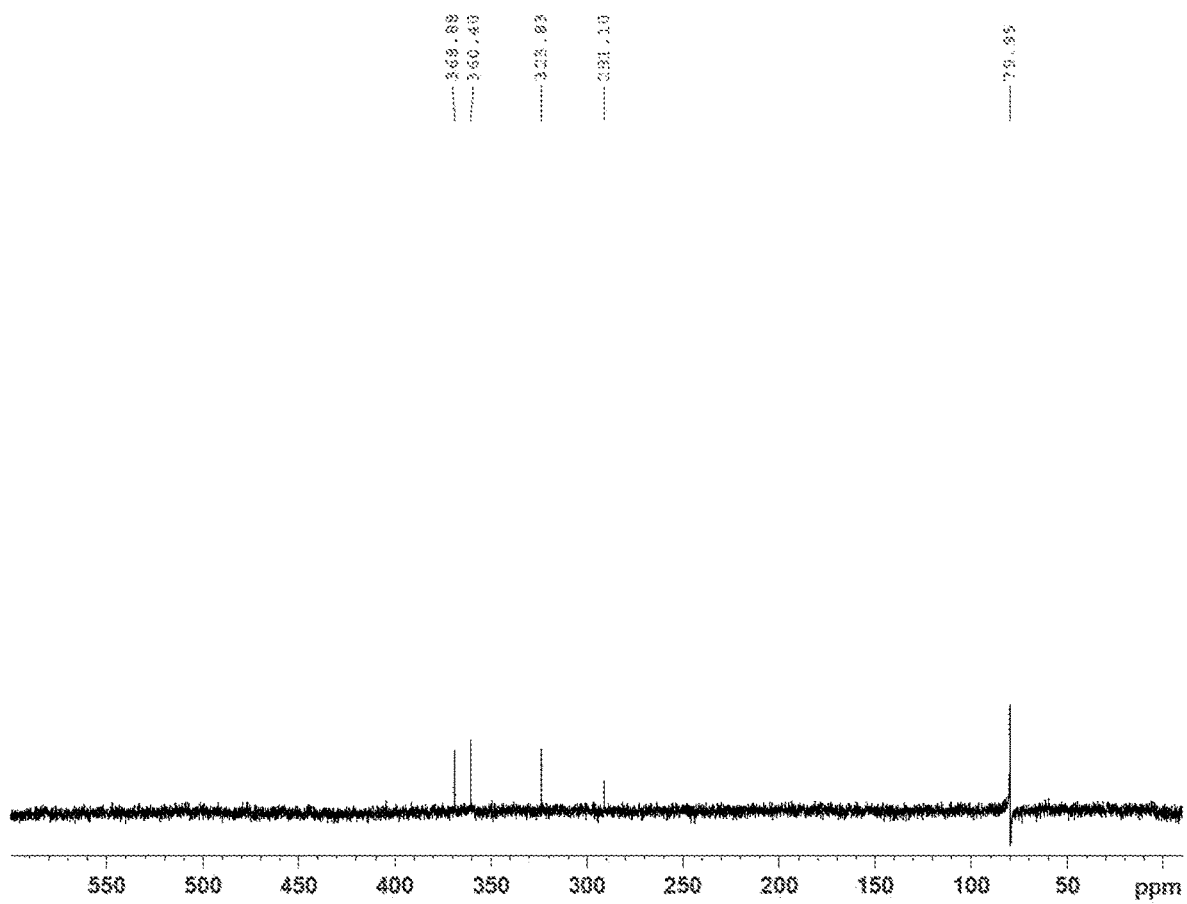
FIG. 12 illustrates the $^{15}$N NMR spectrum of Dihydroxylammonium 5,5'-bistetrazole-1,1'-diolate salt (TKX-50) which was prepared by the examples of the present invention in DMSO.

Please refer to FIG. 10 to FIG. 12. The Dihydroxylammonium 5,5'-bistetrazole-1,1'-diolate salt (TKX-50) which was prepared by the examples of the present invention was subjected to NMR for the structure identification of the synthesized Dihydroxylammonium 5,5'-bistetrazole-1,1'-diolate salt by dissolving the Dihydroxylammonium 5,5'-bistetrazole-1,1'-diolate salt in DMSO solvent and subjecting it to the nuclear magnetic resonance spectrometer ($^1$H-NMR). The obtained chemical shifts are as follows: $^1$H NMR (DMSO-d$_6$, 500 MHZ), δ: 9.647 ppm; $^{13}$C NMR (DMSO-d$_5$, 500 MHZ), δ: 135.45 ppm; $^{15}$N NMR (DMSO-d$_5$, 500 MHZ), δ: 368.88 ppm, 360.4 ppm, 323.83 ppm, 291.1 ppm and 79.95 ppm to match the chemical structure of Dihydroxylammonium 5,5'-bistetrazole-1,1'-diolate (TKX-50).

Given the above, the explosive Dihydroxylammonium 5,5'-bistetrazole-1,1'-diolate (TKX-50) which is prepared by the method for the preparation of an insensitive high enthalpy explosive of the present invention has ideal explosive performance. For example, the calculated detonation velocity is up to 9,698 m/s (the test value is up to 9,537 m/s), an impact sensitivity (IS) is 20 J, and a friction sensitivity (FS) is 120 N. The starting material is inexpensive glyoxal and the final product is obtained through a four-step, one-pot reaction route. The more dangerous intermediate—diazidoglyoxime is solved by the one-pot method without the need of isolation and with 63% yield or more. It may replace the current Octogen (HMX), Hexogen (RDX), and Hexanitrohexaazaisowurtzitane (CL-20) to strengthen the military power for the application of or propellants. In the cyclization reaction of the present invention, the reaction is carried out in the presence of dropwisely added concentrated sulfuric acid to replace hydrochloric gas so no hydrochloric acid gas generator is needed to greatly reduce the amount of waste acid so as to effectively reduce the cost by avoiding using hydrochloric gas steel cylinders which require much safety equipment to meet the legal regulations of toxic substances.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A method for preparing an insensitive high enthalpy explosive via a four-step, one-pot reaction route, comprising:
   (A) performing a chlorination reaction: carrying out the chlorination reaction for 1~4 hours when warming up to 25° C.~50° C., after dissolving glyoxime in at least one of N,N-dimethylformamide, dimethylacetamide and N-methyl-2-pyrrolidone, then adding N-chlorosuccinimide to at least one of the N,N-dimethylformamide, the dimethylacetamide and the N-methyl-2-pyrrolidone with cooling to 0° C.~10° C.;
   (B) performing an azidation reaction: adding sodium azide to at least one of the N,N-dimethylformamide, the dimethylacetamide and the N-methyl-2-pyrrolidone with cooling to −5° C.~5° C. to carry out the azidation reaction for 3 hours at suitable temperature;
   (C) performing a cyclization reaction: adding concentrated sulfuric acid to at least one of the N,N-dimethylformamide, the dimethylacetamide and the N-methyl-2-pyrrolidone to carry out the cyclization reaction for 14~16 hours at suitable temperature before cooling and adding a 40% sodium hydroxide aqueous solution to adjust a pH value to obtain 1,1'-dihydroxy-5,5'-bistetrazole sodium salt tetrahydrate (BTO-Na·4H$_2$O) after filtrating and washing a product with water; and
   (D) performing an ion exchange reaction: dissolving the obtained 1,1'-dihydroxy-5,5'-bistetrazole sodium salt tetrahydrate (BTO-Na·4H$_2$O) in adequate water before dropwisely adding a hydroxylammonium chloride aqueous solution to carry out the ion exchange reaction for 2 hours at suitable temperature to obtain Dihydroxylammonium 5,5'-bistetrazole-1,1'-diolate (TKX-50) after cooling, filtrating and washing a salt product with water.

2. The method for preparing an insensitive high enthalpy explosive via a four-step, one-pot reaction route of claim 1, wherein at least one of the N,N-dimethylformamide and the dimethylacetamide is used as a solvent and a weight ratio of the solvent to the glyoxime is in a range of 5~15:1.

3. The method for preparing an insensitive high enthalpy explosive via a four-step, one-pot reaction route of claim 2, wherein the weight ratio of the solvent to the glyoxime is 10:1.

4. The method for preparing an insensitive high enthalpy explosive via a four-step, one-pot reaction route of claim 1, wherein a mole ratio of added the N-chlorosuccinimide to the glyoxime is in a range of 1~3:1 at a temperature range of 25° C.~45° C. for the chlorination reaction.

5. The method for preparing an insensitive high enthalpy explosive via a four-step, one-pot reaction route of claim 4, wherein the mole ratio of added the N-chlorosuccinimide to the glyoxime is in the range of 1.9~2:1 at the temperature range of 25° C.~35° C. for the chlorination reaction.

6. The method for preparing an insensitive high enthalpy explosive via a four-step, one-pot reaction route of claim 1, wherein a mole ratio of added the sodium azide to the glyoxime is in a range of 1~3:1 at a temperature range of 0° C.~20° C. for the azidation reaction.

7. The method for preparing an insensitive high enthalpy explosive via a four-step, one-pot reaction route of claim 6, wherein the mole ratio of added the sodium azide to the glyoxime is 2:1 at the temperature range of 0° C.~10° C. for the azidation reaction.

8. The method for preparing an insensitive high enthalpy explosive via a four-step, one-pot reaction route of claim 1, wherein a weight ratio of added the concentrated sulfuric acid to the glyoxime is in a range of 7~15:1 at a temperature range of 50° C.~70° C. for the cyclization reaction.

9. The method for preparing an insensitive high enthalpy explosive via a four-step, one-pot reaction route of claim 8, wherein the weight ratio of added the concentrated sulfuric acid to the glyoxime is in the range of 10.5~12.6:1 at the temperature range of 65° C.~70° C. for the cyclization reaction.

10. The method for preparing an insensitive high enthalpy explosive via a four-step, one-pot reaction route of claim 1, wherein the 40% sodium hydroxide aqueous solution is added dropwisely to adjust the pH value to be 9 or more.

11. The method for preparing an insensitive high enthalpy explosive via a four-step, one-pot reaction route of claim 10, wherein the 40% sodium hydroxide aqueous solution is added dropwisely to adjust the pH value to be 10.

12. The method for preparing an insensitive high enthalpy explosive via a four-step, one-pot reaction route of claim 1, wherein a weight ratio of the 1,1'-dihydroxy-5,5'-bistetrazole sodium salt tetrahydrate (BTO-Na.4H$_2$O) to the water is in a range of 1:13~23 and a concentration of 30%~50% of the hydroxylammonium chloride aqueous solution is added dropwisely to carry out the ion exchange reaction at a temperature range of 60° C.~70° C.

13. The method for preparing an insensitive high enthalpy explosive via a four-step, one-pot reaction route of claim 12, wherein the weight ratio of the 1,1'-dihydroxy-5,5'-bistetrazole sodium salt tetrahydrate (BTO-Na.4H$_2$O) to the water is in the range of 1:18~19 and the concentration of 40%~45% of the hydroxylammonium chloride aqueous solution is added dropwisely to carry out the ion exchange reaction at the temperature range of 65° C.~67° C.

* * * * *